(12) United States Patent
Downer et al.

(10) Patent No.: US 9,089,419 B2
(45) Date of Patent: Jul. 28, 2015

(54) SYSTEM TO REDUCE SURFACE CONTACT BETWEEN OPTIC AND HAPTIC AREAS

(75) Inventors: David A. Downer, Fort Worth, TX (US); Drew Morgan, Apalachicola, FL (US); Tu Cam Tran, Grapevine, TX (US); Bobby C. Van Winkle, Midlothian, TX (US)

(73) Assignee: Novartis AG, Basel (CH)

( * ) Notice: Subject to any disclaimer, the term of this patent is extended or adjusted under 35 U.S.C. 154(b) by 180 days.

(21) Appl. No.: 12/573,446

(22) Filed: Oct. 5, 2009

(65) Prior Publication Data

US 2010/0094414 A1    Apr. 15, 2010

Related U.S. Application Data (60) Provisional application No. 61/105,595, filed on Oct. 15, 2008.

(51) Int. Cl.
*A61F 2/16* (2006.01)
*B29D 11/02* (2006.01)

(52) U.S. Cl.
CPC ............ *A61F 2/1613* (2013.01); *B29D 11/023* (2013.01); *A61F 2002/1681* (2013.01); *A61F 2002/1689* (2013.01)

(58) Field of Classification Search
CPC ....... A61F 2/16; A61F 2/1613; A61F 2/1616; A61F 2002/1689; A61F 2002/1681; A61F 2250/0026; A61F 2250/0036; A61F 2250/0053; A61F 2250/0025
USPC ............. 623/6.16, 6.17, 6.25, 6.28, 6.3–6.31, 623/6.4, 6.44, 6.49; 351/161, 164, 165, 168
See application file for complete search history.

(56) References Cited

U.S. PATENT DOCUMENTS

| 3,339,997 | A |   | 9/1967 | Wesley |   |
|---|---|---|---|---|---|
| 4,309,085 | A |   | 1/1982 | Morrison |   |
| 4,377,329 | A | * | 3/1983 | Poler | .......................... 351/160 R |
| 4,401,371 | A |   | 8/1983 | Neefe |   |
| 4,449,257 | A | * | 5/1984 | Koeniger | ..................... 623/6.39 |

(Continued)

FOREIGN PATENT DOCUMENTS

| EP | 0333348 A1 | 9/1989 |
|---|---|---|
| EP | 0445994 A2 | 9/1991 |

(Continued)

OTHER PUBLICATIONS

International Searching Authority, International Search Report, PCT/US2009/060612, Dec. 4, 2009, 2 pages.

(Continued)

*Primary Examiner* — Paul Prebilic (57) ABSTRACT

Embodiments of the present invention provide an intraocular lens with an optic zone having a first surface topology and a haptic zone having a second surface topology. The surface roughness of the haptic zone may be greater than the surface roughness of the optic zone. The surface topology of the optic zone may have a first surface geometry and the surface topology of the haptic zone may have a second surface geometry. The first and second surface geometries may retain lubrication fluid in a space formed therein. The haptics formed by the manufacturing process may have a reduced ability to adhere to the optic zone, such as when the lens is folded or advanced through a cannula.

8 Claims, 5 Drawing Sheets

(56) References Cited

U.S. PATENT DOCUMENTS

| | | | |
|---|---|---|---|
| 4,571,040 A | 2/1986 | Poler | |
| 4,637,697 A * | 1/1987 | Freeman | 351/161 |
| 4,919,130 A | 4/1990 | Stoy et al. | |
| 4,990,159 A * | 2/1991 | Kraff | 623/6.49 |
| 5,074,942 A | 12/1991 | Kearns et al. | |
| 5,178,636 A | 1/1993 | Silberman | |
| 5,405,385 A | 4/1995 | Heimke et al. | |
| 5,549,669 A * | 8/1996 | Jansen | 623/6.49 |
| 6,129,759 A * | 10/2000 | Chambers | 623/6.17 |
| 6,241,766 B1 * | 6/2001 | Liao et al. | 623/6.56 |
| 6,322,589 B1 * | 11/2001 | Cumming | 623/6.44 |
| 6,984,456 B2 * | 1/2006 | Okada et al. | 428/621 |
| 7,625,598 B2 | 12/2009 | Sharma et al. | |
| 7,883,207 B2 * | 2/2011 | Iyer et al. | 351/159.42 |
| 8,608,799 B2 * | 12/2013 | Blake | 623/6.37 |
| 2002/0173846 A1 | 11/2002 | Blake et al. | |
| 2003/0187505 A1 | 10/2003 | Liao | |
| 2004/0119175 A1 | 6/2004 | Reed et al. | |
| 2005/0033422 A1 * | 2/2005 | Zhao et al. | 623/6.17 |
| 2006/0089712 A1 | 4/2006 | Malecaze | |
| 2006/0093846 A1 * | 5/2006 | Chien et al. | 428/520 |
| 2008/0077239 A1 * | 3/2008 | Zickler et al. | 623/6.16 |
| 2008/0220109 A1 * | 9/2008 | Ito et al. | 425/90 |
| 2008/0269890 A1 * | 10/2008 | Simpson et al. | 623/6.46 |
| 2009/0082861 A1 | 3/2009 | Marunaka et al. | |
| 2009/0164008 A1 | 6/2009 | Hong et al. | |
| 2010/0201012 A1 | 8/2010 | Hong et al. | |
| 2011/0098808 A1 | 4/2011 | Kobayashi et al. | |

FOREIGN PATENT DOCUMENTS

| | | |
|---|---|---|
| EP | 0445994 A3 | 4/1992 |
| EP | 1882462 A1 | 1/2008 |
| EP | 2458427 A1 | 5/2012 |
| WO | WO 92/10150 A1 | 6/1992 |
| WO | 01/84216 A1 | 11/2001 |
| WO | 2009/032626 A1 | 3/2009 |
| WO | WO 2010/045305 A1 | 4/2010 |

OTHER PUBLICATIONS

International Searching Authority, Written Opinion of the International Searching Authority, PCT/US2009/060612, Dec. 4, 2009, 6 pages.

European Patent Office, Supplementary European Search Report, Application No. EP 09 82 1163.4, Publication No. EP 2337525, Dated Mar. 6, 2012, 7 pages.

Abstract of JP 02217818A, Published Aug. 30, 1990. Applicant named is Nippon Contact Lens KK.

* cited by examiner

SYSTEM TO REDUCE SURFACE CONTACT BETWEEN OPTIC AND HAPTIC AREAS

This application claims priority to U.S. Provisional Application Ser. No. 61/105,595 filed on Oct. 15, 2008.

TECHNICAL FIELD OF THE INVENTION

The present invention relates to intraocular lenses. More particularly, the present invention relates to providing different surface roughness on the haptics and optic zones of a lens.

BACKGROUND OF THE INVENTION

The human eye can suffer a number of maladies causing mild deterioration to complete loss of vision. Removal of the natural lens may involve making an incision in the eye and augmenting or replacing the natural lens with an intraocular lens.

Intraocular lenses (IOLs) generally include an optic zone and two haptics. The optic zone is the part of the lens the patient sees, and is manufactured to be free of blemishes or manufacturing indicators. The haptics are used to hold the lens in a desired position and orientation. In some situations, the lens may have a single curvature or surface. In other situations, the lens may be toric or aspheric to correct a particular malady.

An IOL may have an optic zone with a diameter of about 6 mm, and the haptics may extend out to about 13-13.5 mm. During implantation of the lens into a patient, an incision of about 2.4-3.0 mm may be formed in the eye. The IOL may be folded and compressed to fit in a cannula with a diameter of approximately 2 mm. One method of folding the IOL may involve folding the haptics inside the optic zone, so that after the IOL is positioned in the eye, the optic zone unfolds and the haptics can be extended and attached as desired.

Manufacturing an intraocular lens generally includes machining an optic pin to a specified roughness on both optic and haptic zones of the pin. Both of these zones are manually polished to a surface roughness on the order of 0.260 microns or less. The finished optic pin is used to injection mold a pair of wafers used to form the IOL.

A common paradigm in the manufacturing of intraocular lenses is the forming of a haptic zone having the same surface roughness as the surface roughness of the optic zone. One result of having the surface roughness for a haptic zone being the same as the surface roughness of the optic zone is the possibility for the haptic zone to adhere to the optic zone. The adherence of a haptic to the optic zone may be likened to the adherence exhibited between contact surfaces when two smooth or polished surfaces are in contact. The situation may be worse if the contact surfaces are wet. For example, when two glass panes are in contact, separation may be possible only by sliding one pane relative to the other or applying significant forces to pull them apart.

With respect to haptics, the options for a surgeon to separate a haptic from an optic zone may be more limited. In some situations, a haptic that has adhered to the optic zone may release after a short time without intervention by the surgeon, although the surgeon must wait for the haptic to separate from the optic zone. In some situations, a haptic may be adhered to the optic zone but may be released by the surgeon intervening to separate the haptic from the optic zone, such as by using tools to pull the haptic away from the optic zone. In some situations, a haptic may be adhered to the optic zone such that the surgeon is forced to remove the lens and insert a new lens. In these embodiments, there is the danger that the surgeon may damage the bag or other portion of the eye during the removal process, and there is no guarantee that the replacement lens will not have the same difficulties.

SUMMARY OF THE INVENTION

Embodiments of an intraocular lens may include an optic zone having a first surface topology and a haptic having a second surface topology, wherein the second surface topology reduces the ability for the haptic to adhere to the optic zone. In some embodiments, the first surface topology comprises a first surface roughness and the second surface topology comprises a second surface roughness greater than the first surface roughness. The second surface roughness may be at least two times greater than the first surface roughness. In some embodiments, the first surface topology comprises a first surface geometry and the second surface topology comprises a second surface geometry different than the first surface geometry. The first surface geometry and the second surface geometry may form a space between the haptic and the optic zone during insertion of the intraocular lens such that the space formed by the haptic and the optic zone retains lubrication fluid. The second surface geometry may have one or more positive features or negative features.

One method of manufacturing an intraocular lens may include forming an optic pin. Forming an optic pin may include forming an optic zone having a first surface topology corresponding to an optic zone in an intraocular lens and forming a haptic zone having a second surface topology corresponding to a haptic in the intraocular lens, wherein the second surface topology reduces the ability for the haptic to adhere to the optic zone. In some embodiments, forming an optic zone having a first surface topology comprises forming a first surface roughness, and forming a haptic zone having a second surface topology comprises forming a second surface roughness greater than the first surface roughness. In some embodiments, the second surface roughness is at least two times greater than the first surface roughness. In some embodiments, forming an optic zone having a first surface topology comprises forming a first surface geometry. Forming a haptic zone having a second surface topology comprises forming a second surface geometry such that a space is formed between the haptic and the optic zone during insertion of the lens into a patient. In some embodiments, forming a haptic zone having a second surface topology comprises rotating the optic pin about a z-axis and moving a cutting tool across the optic pin in one or more of the x-direction, the y-direction, and the z-direction. In some embodiments, forming a haptic zone having a second surface topology comprises rotating the optic pin about a z-axis and moving a cutting tool across the optic pin based on a wavelength and amplitude. In some embodiments, forming a haptic zone having a second surface topology comprises rotating the optic pin about a z-axis and moving a cutting tool across the optic pin based on a radius and an angle.

One method for inserting an intraocular lens in a patient may include making an incision in the eye, inserting a cannula into the incision, and advancing an intraocular lens through the cannula into the eye. The intraocular lens may include an optic zone having a first surface topology and a haptic having a second surface topology such that the second surface topology reduces the ability for the haptic to adhere to the optic zone during advancement of the intraocular lens through the cannula. In some embodiments, advancing the intraocular lens through the cannula comprises folding the haptic inside the optic zone. In some embodiments, the method may include injecting lubrication fluid inside the folded intraocular lens. The first surface geometry and the second surface geometry form a space to retain the lubrication fluid during advancement of the intraocular lens through the cannula. In some embodiments, the first surface topology comprises a toric or aspheric surface. In some embodiments, the first surface topology comprises a diffractive zone.

Embodiments of an optic pin may include an optic zone having a first surface roughness and a haptic zone having a second surface roughness. The optic pin may be used to manufacture wafers for forming an intraocular lens having an optic zone with a first surface roughness and a haptic having a second surface roughness.

Embodiments of an optic pin may include an optic zone having a first surface geometry and a haptic zone with a second surface geometry. The optic pin may be used to manufacture wafers for forming an intraocular lens having an optic zone with a first surface geometry and a haptic having a second surface geometry.

In some embodiments, a method for implanting an intraocular lens may include folding the haptics of the lens inside the optic zone of the lens, wherein the haptics may have a surface roughness greater than the surface roughness of the optic zone to prevent adherence of the haptics to the optic zone.

In some embodiments, a method for implanting an intraocular lens may include folding the haptics of the lens inside the optic zone of the lens, wherein the haptics may have a surface geometry to prevent adherence of the haptics to the optic zone. Embodiments of IOLs may be soft-foldable lenses. The IOLs may be folded for insertion into a cannula. Microfissures or other features of the surface geometry of the haptics may help retain lubrication fluid between various portions of the IOL to inhibit the haptics from sticking to each other or the optic zone.

Other objects and advantages of the embodiments disclosed herein will be better appreciated and understood when considered in conjunction with the following description and the accompanying drawings.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

The intraocular lens (IOL) and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

Embodiments of the present disclosure provide an intraocular lens in which the haptics may be manufactured having a different surface topology than the optic zone of the IOL.

A method for manufacturing an intraocular lens may include manufacturing an optic pin having an optic zone surface topology and a haptic zone surface topology. A method for manufacturing an optic pin may include machining the surface topology of the optic zone to have a first surface roughness and machining the surface topology of the haptic zone to have a second surface roughness. The surface roughness of an optic pin is generally the product of the speed and feed rate of the machine. Thus, for a given speed and feed rate, a surface roughness will be formed on the optic pin. By increasing the speed and/or decreasing the feed rate, the surface roughness will be lower. Conversely, by decreasing the speed and/or increasing the feed rate, the surface roughness will increase. In some embodiments, the surface topology of an optic pin may be manufactured by machining the optic zone at a first speed and feed rate and machining the surface topology of the haptic zone at a different speed and feed rate such that the surface roughness of the haptic zone is higher than the surface roughness of the optic zone.

The surface topology of an optic zone of an intraocular lens should be free of indentations, scratches, nicks, and other blemishes that may negatively affect vision in a patient. In some embodiments, the surface topology of the optic zone of an optic pin may be manufactured such that the optic zone of an intraocular lens formed by the optic pin has a desired surface roughness. Furthermore, as known to those skilled in the art, the surface roughness for an optic zone is ideally minimized to provide improved visibility for the patient. In some embodiments, the surface topology of the optic zone of an intraocular lens may be manufactured to have a surface roughness of 0.260 microns or less. Embodiments of an IOL may be formed with minimal surface roughness in the optic zone. In some embodiments, an IOL may have a surface topology of the optic zone formed with diffractive zones or other features known in the art.

In some embodiments, the surface topology of the haptic zone of an optic pin may be manufactured such that the surface topology of a haptic of an intraocular lens formed by the optic pin has a desired surface roughness. The ratio of the surface roughness of a haptic and the surface roughness of an optic zone may determine whether the surface topology of the haptic will adhere to the surface topology of the optic zone during insertion of the intraocular lens into the patient. The ratio of surface roughness for the surface topology of the haptic and the surface roughness of the surface topology of the optic zone may be expressed as a factor, F. Namely, $$F = \left(\frac{R_{haptic}}{R_{optic}}\right)$$

where $R_{haptic}$ is the surface roughness of the haptic and $R_{optic}$ is the surface roughness of the optic zone. In some embodiments, F may be greater than 2 (i.e., the surface roughness for a haptic zone of an optic pin may be a factor of 2 (two) or more times the surface roughness for an optic zone). In some embodiments, F may be greater than 3 (three). Thus, when haptics are formed from the haptic zone, the haptics may have a surface roughness that differs from the surface roughness of the optic zone.

A comparison of the amount of time needed to separate the haptics from the optic zone may illustrate the effect that disparate surface roughness can have on the ability for haptics to adhere to the optic zone. Table 1 lists results performed for a control group (F=1) and two test groups: Test group 1 is for an optic pin in which the lathe was turned at 20% feed; and Test group 2 is for an optic pin in which the lathe was turned at 30% feed.

TABLE 1

| Group | PV | Release time |
|---|---|---|
| Control | 0.2616 | 1 min 30 sec |
| Test 1 | 0.5006 | 1 sec |
| Test 2 | 3.443 | 1 sec |

Test group 1 and Test group 2 both required about a second for the haptics to separate from the optic zone, while the Control group (using the prior art paradigm) may require 90 seconds to separate. From the results listed in Table 1, it may be appreciated that increasing the surface roughness of the haptics may decrease the time needed for the haptics to separate from the optic zone.

Figure 1A:
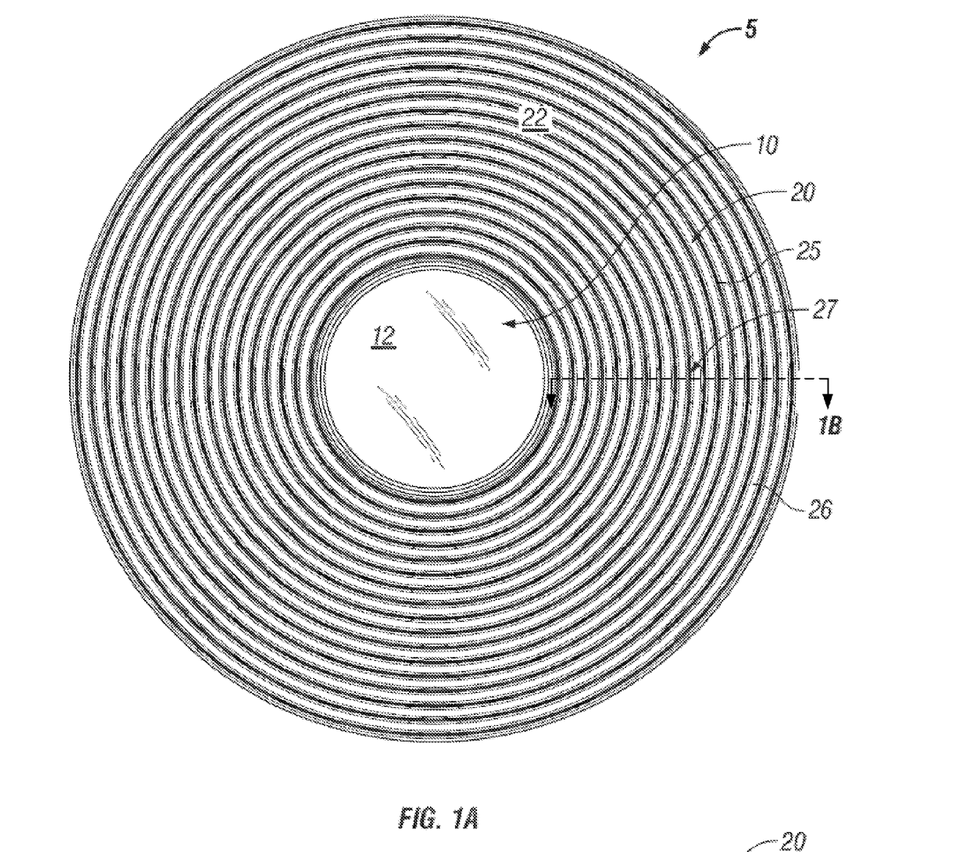
FIG. 1A is a diagrammatic representation of one embodiment of an optic pin having one embodiment of a surface geometry.
Figure 1B:
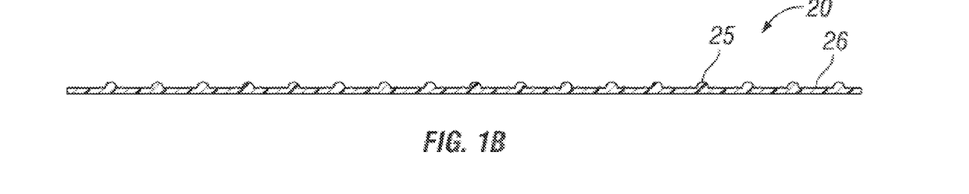
FIG. 1B depicts a close-up side view of the surface topology of the embodiment of the optic pin of FIG. 1A.

A method for manufacturing an intraocular lens may include manufacturing an optic pin to have different surface geometries for the surface topology of the optic zone and the surface topology of the haptics to reduce the ability of the haptics to adhere to the optic zone during insertion of the lens into the patient. FIGS. 1A and 1B depict diagrammatic top and close-up cross-sectional views of one embodiment of optic pin 5 used for manufacturing an intraocular lens. Optic pin 5 may include optic zone 10 having surface topology 12 with a first surface geometry and haptic zone 20 having surface topology 22 with a second surface geometry.

Optic zone 10 may be formed to replace the natural lens or to correct maladies in the natural lens. Thus, in some embodiments, surface topology 12 of optic zone 10 of optic pin 5 may be formed to have a surface geometry with a toric profile, an aspheric profile, or some other profile known to those skilled in the art for correcting astigmatism, cataracts, and other eye maladies without departing in scope from the present disclosure.

In some embodiments, optic pin 5 may have surface topology 22 of haptic zone 20 formed with a surface geometry distinct from the surface geometry of surface topology 12 of optic zone 10. In some embodiments, optic pin 5 may be formed such that the surface geometry of haptic zone 20 has features that extend in a positive z-direction relative to the surface of optic zone 10. In some embodiments, optic pin 5 may be formed such that the haptic zone surface geometry has features that extend in a negative z-direction relative to the surface of optic zone 10. For example, the surface geometry of optic pin 5 may be formed to have raised ring 25 (i.e., a positive feature) or groove 26 (i.e., a negative feature). In a 2-D drawing, a positive feature may appear to be coming out of the paper, and a negative feature may appear to be going into the paper.

In some embodiments, the surface geometry of haptic zone 20 may include continuous positive or negative features. A continuous feature may extend axially or radially, and may terminate at the interface between optic zone 10 and haptic zone 20, the outer edge of haptic zone 20, or at some point in between. For example, FIG. 1B depicts positive features (e.g. raised rings 25) and negative features (e.g., grooves 26) that are continuous axially. Rings 25 have rounded tops. FIG. 1A further depicts positive features (e.g. ridges 27) that are continuous radially from the interface between optic zone 10 and haptic zone 20 to the outer edge of haptic zone 20. Ridges 27 can be shorter raised areas higher than rings 25 that can be placed in a desired pattern about haptic zone 20. In FIG. 1A, for example, ridges 27 are placed every 45 degrees. In some embodiments, surface topology 22 of haptic zone 20 may further have a selected surface roughness to further reduce the ability for a haptic to adhere to the optic zone of a lens. Thus, each of rings 25 may have a surface roughness which may or may not be the same as other rings 25, grooves 26, or ridges 27. Haptics having a variety of shapes can be formed from the haptic zone. By way of example, but not limitation, one haptic shape is shown in U.S. Pat. Nos. 6,261,321 and 5,716,403, each of which are incorporated by reference herein.

Figure 2A:
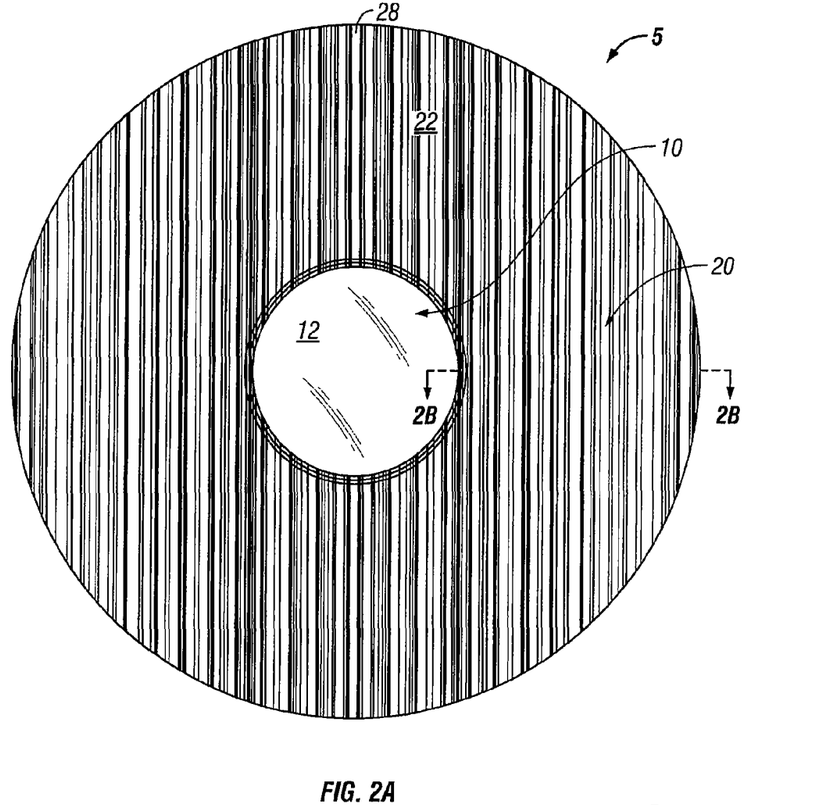
FIG. 2A is a diagrammatic representation of one embodiment of an optic pin having one embodiment of a surface geometry.
Figure 2B:
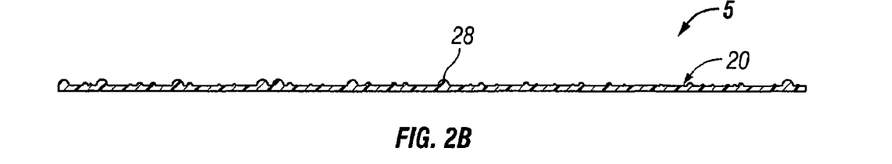
FIG. 2B depicts a close-up side view of the surface topology of the embodiment of the optic pin of FIG. 2A.

FIGS. 2A and 2B depict diagrammatic top and close-up cross-sectional views of one embodiment of optic pin 5 having surface topology 22 of haptic zone 20, in which the surface geometry of haptic zone 20 is formed with straight lines 28. Lines 28 may be formed having various thickness, uniform thickness, uniform height, various heights, and other parameters. Optic pin 5 depicted in FIG. 2A illustrates one embodiment produced by a method of manufacturing in which the cutting tool is constrained to move in the x-direction, can move in the z-direction, but cannot move in the y-direction.

Figure 3A:
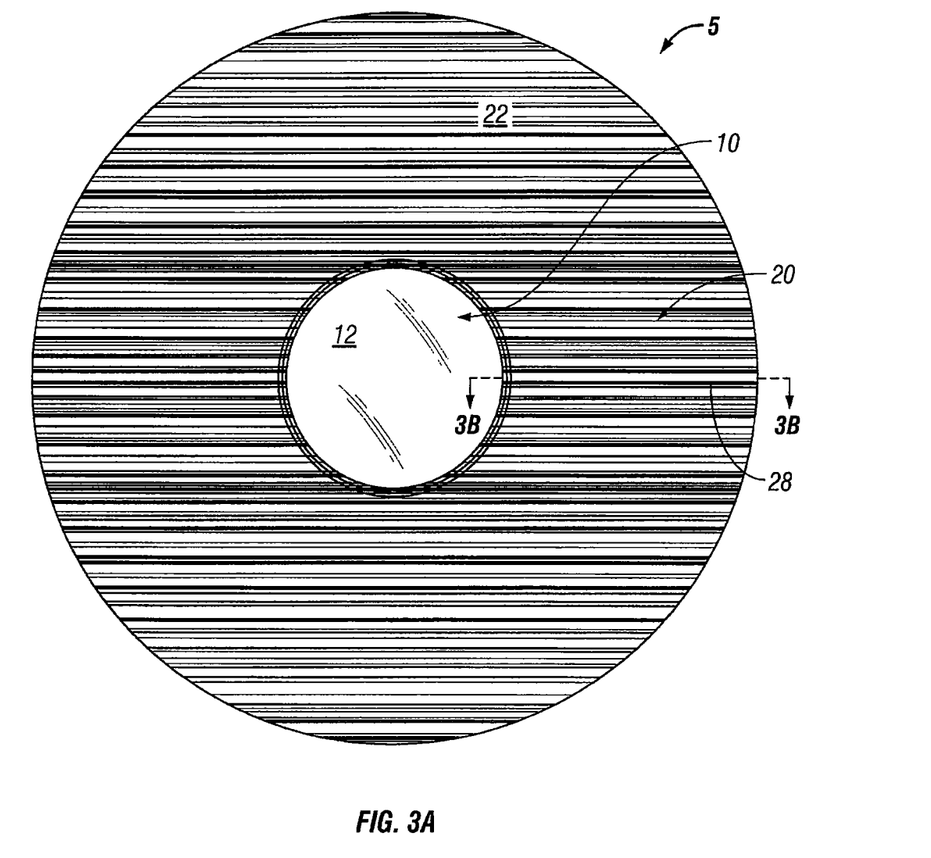
FIG. 3A is a diagrammatic representation of one embodiment of an optic pin having one embodiment of a surface geometry.
Figure 3B:
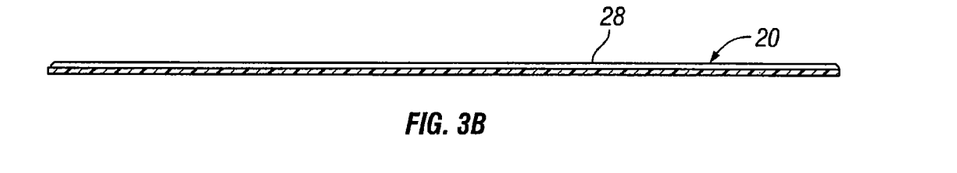
FIG. 3B depicts a close-up side view of the surface topology of the embodiment of the optic pin of FIG. 3A.

FIGS. 3A and 3B depict diagrammatic top and close-up cross-sectional views of one embodiment of optic pin 5 having surface topology 22 of haptic zone 20, in which the surface geometry of haptic zone 20 is formed with straight lines 28. Lines 28 may be formed having various thickness, uniform thickness, uniform height, various heights, and other parameters. Optic pin 5 depicted in FIG. 3A illustrates one embodiment produced by a method of manufacturing in which the cutting tool is constrained to move in the y-direction, can move in the z-direction, but cannot move in the x-direction.

Figure 4A:
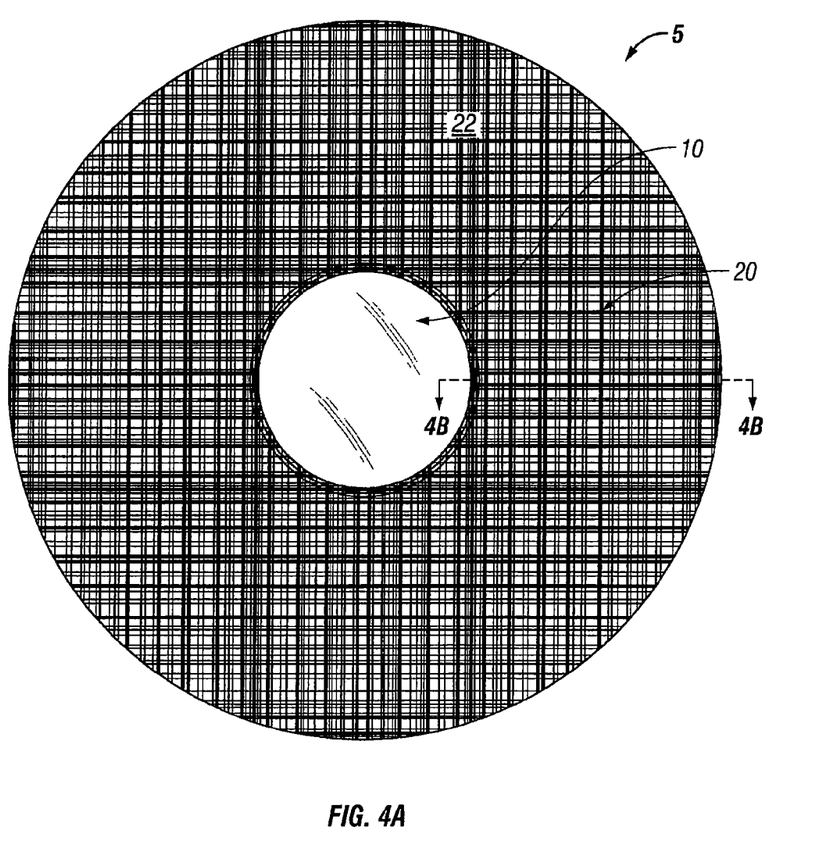
FIG. 4A is a diagrammatic representation of one embodiment of an optic pin having one embodiment of a surface geometry.
Figure 4B:
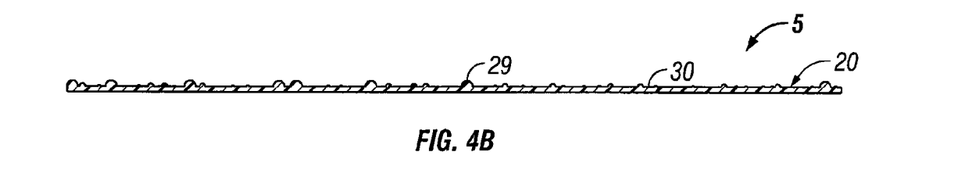
FIG. 4B depicts a close-up side view of the surface topology of the embodiment of the optic pin of FIG. 4A.

FIG. 4A depicts one embodiment of optic pin 5 in which the surface topology 22 has a plurality of raised areas 29 and recessed areas 30. Raised areas 29 and recessed areas 30 may be curvilinear or rectilinear or some combination thereof. FIG. 4B depicts a close-up view of the embodiment of optic pin 5 depicted in FIG. 4A, illustrating that haptic zone 20 may include positive and negative features.

Figure 5A:
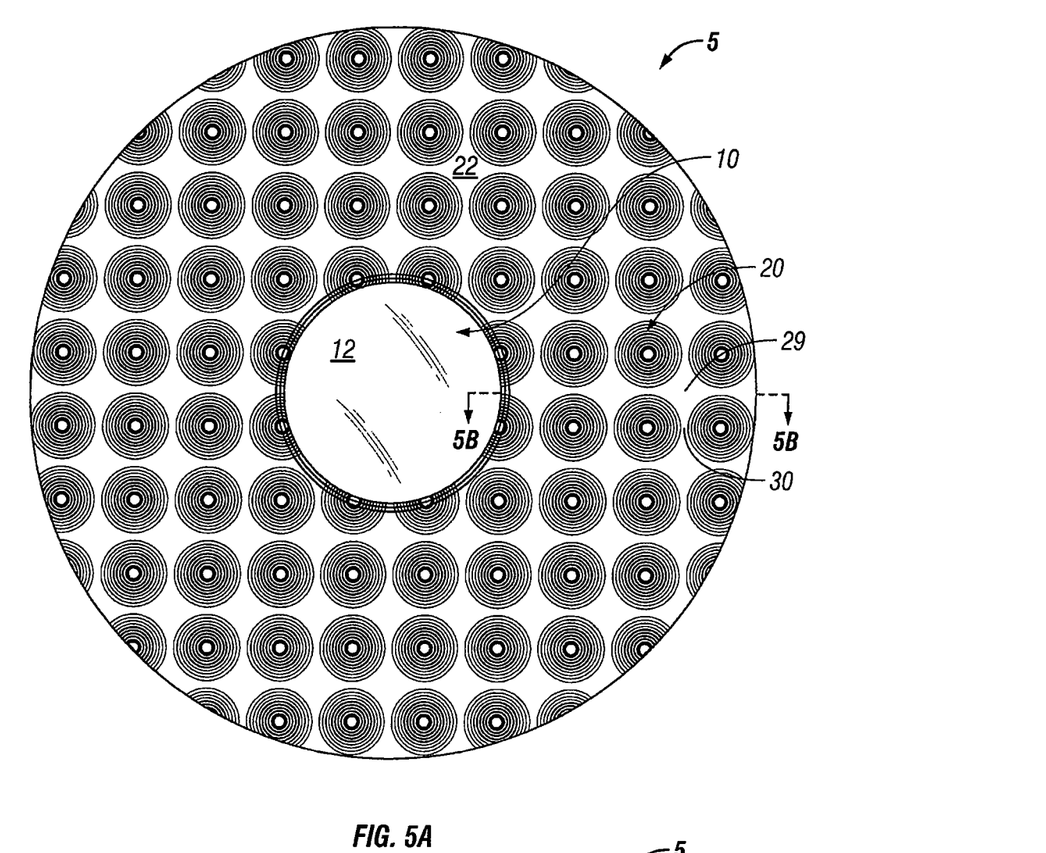
FIG. 5A depicts a view of one embodiment of the surface topology of an optic pin.
Figure 5B:
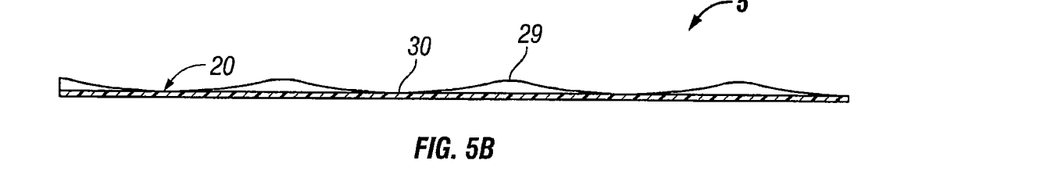
FIG. 5B depicts a close-up side view of the surface topology of the embodiment of the optic pin of FIG. 5A.

FIG. 5A depicts a view of one embodiment of surface topology 22 of optic pin 5, in which the surface topology 22 has a plurality of raised areas 29. FIG. 5B depicts a close-up side view of the embodiment of optic pin 5, illustrating that the surface geometry of haptic zone 20 may be constrained to have only positive features.

A method of manufacturing optic pin 5 having optic zone 10 having surface topology 12 with a first surface geometry and the haptic zone 20 having a second surface geometry may include positioning a piece of stock in a machine and selecting operating parameters of the machine. In some embodiments, a machine may be selected to provide rotation of the piece of stock in the x-y plane and further operable to move the head of a cutting tool in x, y and z directions. The tool may be operable to rotate the piece of stock at a desired rotational velocity and position the head of the cutting tool based on a frequency and amplitude, angle and arclength, or x, y and z coordinates to ensure precise positioning of the cutting head. In one embodiment, freeform machining may be employed to generate tool travel synchronous with part rotation to form a first surface geometry and a second surface geometry.

Referring still to FIGS. 1AB, 2A-B, 3A-B, 4A-B, 5A and 5B, FIG. 1A depicts a view of one embodiment of optic pin 5 in which surface topology 22 of optic pin 5 may be manufactured with the head of the cutting tool moving at a wavelength of 0.4 mm and at amplitude of 0.1 mm for a desired feed rate and speed.

FIGS. 2A and 3A depict views of one embodiment of optic pin 5 in which surface topology 22 of optic pin 5 is manufactured with the head of the cutting tool moving in the x-direction and in the y-direction, respectively. Those skilled in the art will appreciate that by changing the operating parameters of the machine, the surface geometry of haptic zone 20 may have different characteristics. The characteristics may vary by axial or radial position, may be symmetric about an axis or plane, and may repeat or may be independent.

Optic pin 5 depicted in FIG. 4A illustrates one embodiment produced by a method of manufacturing in which the cutting tool is free to move in the x- and y-directions and can move in the positive or negative z-direction. Thus, surface topology 22 of optic pin 5 depicted in FIG. 4A may be the result of combining lines 28 in FIG. 2A and FIG. 3A such that, at some points in haptic zone 20, lines 28 may combine to form positive features 29 or negative features 30 and, at other points, lines 28 may combine to cancel each other.

Optic pin 5 depicted in FIG. 5A illustrates one embodiment produced by a method of manufacturing in which the cutting tool is free to move in the x- and y-directions and can move in the positive z-direction. FIG. 5B depicts a close-up side view of surface topology 22 of the embodiment of optic pin 5, illustrating that the surface topology of optic pin 5 may be manufactured with the head of a cutting tool constrained to have only positive z values relative to optic zone 10.

An advantage to having different surface geometries may be the ability for lubrication fluid to be retained between haptics and the optic zone of an intraocular lens during insertion of the lens into the patient. Microfissures or cavities in the haptic may provide enough volume to retain the lubrication fluid to reduce the ability of the haptics to adhere to the optic zone.

Another advantage to having different surface geometries may be a reduced likelihood of the haptics leaving impressions in the optic zone. If the optic zone is a continuous piece of material and the haptic is formed with the surface geometry of haptic zone 20 having thinner or otherwise more deflectable features, the haptic (and not the optic zone) may deform during the insertion process. Thus, the surgeon does not need to wait to see if the deformation will release from the material, but may instead insert the intraocular lens as long as no deformation is detected in the optic zone. Depending on the temperature of the operating room, the time saved may be several seconds or longer. However, those skilled in the art will appreciate that even a small time delay due to the haptics adhering to the optic zone may increase the chance of the eye sustaining further injury.

From the foregoing description, those skilled in the art will appreciate that optic pin 5 may be manufactured having the surface topology of optic zone 10 with a first surface roughness or first surface geometry and haptic zone 20 with a surface topology with a second surface roughness greater than the first surface roughness or the surface geometry of haptic zone 20 that is different from the optic zone surface geometry.

While the intraocular lens of the present disclosure has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

What is claimed is:

1. An intraocular lens comprising:
   an optic zone, configured to replace a natural lens or to correct a malady in the natural lens of an eye, having a first surface topology; and
   a haptic, configured to hold the intraocular lens in the eye, having a second surface topology, wherein the second surface topology reduces the ability for the haptic to adhere to the optic zone,
   wherein the second surface topology comprises one or more continuous features, wherein the one or more continuous features comprise:
      a first plurality of rings, wherein the first plurality of rings are regularly spaced, concentric, raised circular rings each having a same first height;
      a second plurality of rings, wherein the second plurality of rings are concentric, raised circular rings each having a same second height;

wherein the first height is greater than the second height and wherein the first plurality of rings is concentric with the second plurality of rings; and wherein the first plurality of rings and the second plurality of rings comprise a repeating pattern, along the surface of the hapic, comprising:

a ring of the first plurality of rings;
two rings of the second plurality of rings;
a ring of the first plurality of rings;
two rings of the second plurality of rings.

2. The intraocular lens of claim 1, wherein the first surface topology comprises a first surface roughness and the second surface topology comprises a second surface roughness greater than the first surface roughness.

3. The intraocular lens of claim 2, wherein the second surface roughness is at least two times greater than the first surface roughness.

4. The intraocular lens of claim 1, wherein the first surface geometry and the second surface geometry form a space between the haptic and the optic zone during insertion of the intraocular lens, wherein the space formed by the haptic and the optic zone retains lubrication fluid.

5. The intraocular lens of claim 1, wherein the haptic is configured to hold the intraocular lens in a desired position and orientation.

6. The intraocular lens of claim 1, wherein the haptic is configured to be folded inside the optic zone as the intraocular lens is compressed for insertion into the eye and wherein the second surface topology of the haptic forms a space between the haptic and the optic zone during insertion of the lens into the eye.

7. The intraocular lens of claim 6, wherein the optic zone is configured to unfold in the eye.

8. The intraocular lens of claim 1, wherein the first plurality of rings have rounded tops.

\* \* \* \* \*